United States Patent [19]

Verdini et al.

[11] Patent Number: 5,116,946
[45] Date of Patent: May 26, 1992

[54] SYNTHETIC, IMMUNOLOGICALLY ACTIVE PEPTIDES USEFUL FOR THE PREPARATION OF ANTIMALARIAL VACCINES

[75] Inventors: Antonio S. Verdini, Monterotondo; Antonello Pessi; Fabio Bonelli, both of Rome, all of Italy

[73] Assignee: Eniricerche S.p.A., Milan, Italy

[21] Appl. No.: 358,932

[22] Filed: May 30, 1989

[30] Foreign Application Priority Data

Jun. 8, 1988 [IT] Italy ................... 2088 A/88

[51] Int. Cl.$^5$ .......................... C07K 3/00; A61K 37/02
[52] U.S. Cl. ..................................... 530/300; 530/350
[58] Field of Search .............. 530/350, 324, 329, 327, 530/330, 300; 424/88; 514/19

[56] References Cited

PUBLICATIONS

Gibson et al., Predicted Conformations for the Immunodominant Region of the CP of the Human Malaria Parasite Plasmodium falciparum PNAS 86:5649–5653, 1986.

Dayhoff et al., A Model of Evolutionary Change in Proteins Atlas of Proteins Sequence & Structure 1972, vol. 5, 89–99.

Primary Examiner—Christine Nucker
Assistant Examiner—H. Sidberry
Attorney, Agent, or Firm—Shea & Gould

[57] ABSTRACT

Synthetic peptides constituted by at least two repeating, consecutive units of asparaginyl-proline $(Asn-Pro)_n$ sequence, are described.

The peptides are powerful immunogens, capable of inducing in laboratory animals the formation of a high concentration of antibodies capable of reacting both with the $(Asn-Pro)_n$ peptides, and with the immunodominant epitope of the circumsporozoite protein of Plasmodium falciparum.

The peptides, which can be obtained in a pure form by chemical synthesis, are particularly useful for preparing antimalarial vaccines and diagnostic kits for the determination of malaria in man.

5 Claims, No Drawings

SYNTHETIC, IMMUNOLOGICALLY ACTIVE PEPTIDES USEFUL FOR THE PREPARATION OF ANTIMALARIAL VACCINES

The present invention relates to novel synthetic, immunologically active peptides useful in the sector of malaria.

More particularly, the present invention relates to novel synthetic peptides capable of inducing in mammals a high-titre and specific antibody reaction against the immunodominant epitope of the circumsporozoitic protein of *Plasmodium falciparum*.

Malaria, caused by a protozoan of Plasmodium genus, is presently among the most serious parasitical diseases in man.

In fact, this disease is estimated to strike, each year, from 100 to 200 million individuals, causing in the first infancy a mortality rate which may reach 50% of cases.

Of the four Plasmodium species infective in man, the most common ones are: *P. vivax* and *P. falciparum*.

This latter, in particular, causes most of morbidity and mortality associated with malaria, and owing to this reason, a vaccine against such an etiological agent is particularly desirable. The infection begins in man with the introduction, by the mosquito, of sporozoites, which rapidly reach the hepatic cells. Inside these latter, each sporozoite generates 20,000 or more merozoites, each of which, after leaving the hepatic cell, is capable of infecting an erythrocyte. Inside the erythrocyte, the parasite reproduces itself asexually, from rings into schizonts.

The mature schizont contains single merozoites, which are capable of invading further erythrocytes.

Such a cycle of repeated breakage of the erythrocyte by the asexual parasites causes the clinical manifestations.

Some merozoites, instead of continuing to proliferate, differentiate into gametocytes, which represent the infecting form for mosquitos.

The complex structure and the vital cycle of the malarial parasites have made it difficult, to date, to solve the problem of an efficacious antimalarial vaccine.

Malarial parasites, in fact, develop according to a multi-step cycle, and present to the host organism an extremely large number of antigenic components, and each form of parasite development contains step-specific antigens different from one another.

In their efforts aiming at identifying plasmodial protective antigens, researchers addressed their interest towards those of them which are exposed to the immunitary system and are present at the surface of the parasite, or on the membrane of the infected erythrocyte. Particularly interesting was the study of the sporozoites of Plasmodium, in that the preparation of an antisporozoite vaccine, if completely efficacious, is capable of preventing the development of plasmodium in the host, and of hence inducing a sterile immunity.

Attempts for an antisporozoite vaccination on animals and man were carried out by using sporozoites of *P. falciparum* and *P. vivax* irradiated with X-rays, with a non-strain-specific protective immunity against malaria being obtained.

However, a so-formulated vaccine appears to be not very suitable for a large-scale application, both owing to the limited availability of the sporozoites, and to their unstability.

The use of monoclonal antibodies led to the identification of the major surface protein of the sporozoites of *P. berghei* [N. Yoshida, R. S. Nussenzweig et al. (1980) Science 209, 711] and of other protozoans infective for animals and man, including *P. falciparum* [F. Santoro et al. (1983) J. Biol. Chem. 258, 3341].

This protein, which is referred to as the "circumsporozoitic protein" ("CSP") completely coats the surface of the sporozoite, and induces a specific antibody reaction, which confers a protection against malarial infections.

Recently, in patent application EP 166 410, the cloning and the sequencing was disclosed of the gene codifying for the CS protein of *P. falciparum*, and the matter of fact was evidenced, that said protein contains in its central region, 37 repetitions of the tetrapeptidic sequence —asparagine—alanine—asparagine—proline—
(NANP)

and 4 repetitions of the tetrapeptidic sequence

—asparagine—valine—aspartic acid—proline—
(NVDP)

three of which alternate at the N-chain end with the NANP sequence, so as to form:

-NANP-NVDP-NANP-NVDP-NANP-NVDP-NANP-

Experimental tests carried out by R. Nussenzweig et al. [Science, 234, 1349–1356 (1986): Am. J. Trop. Med. Hyg. 34, 678–688 (1986)] demonstrated that:

1) the region of the repetitions contains the immunodominant epitope of CSP;
2) the immunodominant epitope is defined by three consecutive (NANP)$_3$ repetitions;
3) antisporozoitic mono- and polyclonal antibodies recognize (NANP)$_3$, and anti-(NANP)$_3$ antibodies react with the sporozoites and prevent, in vitro, them from entering the hepatocyte;
4) antibodies present in the serum of a volunteer, vaccined with irradiated sporozoites, and protected from malaria, were mainly directed against (NANP)$_3$;
5) by using (NANP)$_3$ as the antigen in an immunoradiometric assay, it was observed that the peptide reacts well with the sera of randomly selected individuals living in endemic areas;
6) (NANP)$_3$ is present in all of the strains of *P. falciparum* obtained from mosquitos captured in all continents;
7) the immunization of rabbits or mice with (NANP)$_3$ conjugated with albumin of bovine serum induces the formation of antibodies capable of neutralizing the infectivity of the sporozoite.

It was furthermore observed that a polypeptide containing 32 repeated NANP sequences is a powerful immunogen in mouse, and induces antibodies.

All these results indicate hence that synthetic polypeptides containing the repetitions of CS can be regarded as promising candidates for the development of an antimalarial vaccine.

Clinical tests on volunteers were carried out with the (NANP)$_3$-tetanus toxoid conjugate, and with (NANP)$_{32}$ bonded to a peptidic segment containing the first 32 aminoacids coded by the gene for resistance to tetracycline [W. R. Ballau et al. Lancet, 1277–1281

(1987); D. A. Herrington et al. Nature, 328, 257–259 (1987)].

However, the use of "carrier" proteins or polypeptides involves at least two potential risks:
(1) inasmuch as such "carrier-peptide" vaccines do not simulate the antipeptide T cells (the reaction of the T cells is directed against the antigen determinants of the "carrier"), the vaccinated patients could possibly not benefit by the natural "boost" caused by the inoculation of the sporozoites by the mosquito; and
(2) a suppression could possibly occur of the immunitary anti-(NANP)$_3$-peptide response induced by the "carrier" (carrier-induced epitopic suppression), in that most individuals have already been vaccined against tetanus.

Therefore, in the art other processes were proposed for the preparation of immunologically active peptides containing said repeating sequences.

So, e.g., the co-pending U.S. patent application No. 850 135 discloses and claims sequential peptides constituted by the (NANP) tetrapeptide repeated n times, preferably 40 times, obtained by means of a polycondensation process.

(NANP)$_{40}$ is a powerful immunogen, and does not require conjugation with a carrier protein or polypeptide.

The produced IgG's specifically react with an extract of mosquitos infected by P. falciparum and, in vitro, stimulate a proliferative reaction of the T cells.

However, both in vivo and in vitro, the results obtained clearly indicate that the response of the T cells specific for repeated (NANP) sequences is genetically limited [G. Del Giudice et al., J. Immunol. 137, 2952–2955 (1986); A. R. Togna et al., J. Immunol. 137, 2956–2960 (1986)].

More exactly, such a response is tied to the presence of the $1_b$ allele of the Ia region of mouse Major Histocompatibility Complex (H-2).

The above reported results induced therefore the researchers to think that synthetic vaccines of (NANP)$_{40}$ type might be not very suitable for conferring a protective immunity to man in that, even if in man the immunitary response was under genetic control, the possible production of protective antibodies under natural "boosting" conditions, i.e., caused by the bite of infected mosquitos, would occur in "responder" individuals only. It is well known in fact that, in order that an antibody response against whatever immunogen may take place, a cellular cooperation is necessary between the lymphocytes of T-helper type, and the antibody-producer B-lymphocytes, each activated by the recognition of its epitopes.

Therefore, a vaccine efficacious against malaria should comprise antigens containing epitopes capable of both stimulating the T cells to help the B cells to produce anti-NANP antibodies, and of causing the T cell proliferation which is essential for the antibody-independent cellular immunity to be established.

By using the sequential (NANP)$_{40}$ polypeptide as the model in the configurational investigations in solution, in water the polypeptidic chains were found to lack a secondary structure, and to be essentially disordered and highly flexible [A. S. Verdini, 1st Conference Jacques Monod: "Molecular Approaches to Vaccination against Parasitic Diseases (Approcci Molecolari alla Vaccinazione contro le Mallattie Parassitarie)" Roscoff, France, Sep., 1–4 (1987)].

Experimental tests of both unidimensional and bidimensional protonic Nuclear Magnetic Resonance showed furthermore that the structural disorder is probably tied to the several possible configurational options of the polypeptidic chain at the level of NPN and NPNA segments.

Structures of $\gamma_1$ type of NPN sequences, and of $\beta$-turn I and II types for the NPNA sequences were experimentally observed in solvent mixtures of water/methanol and water/trifluoroethanol in such models as (NANP)$_2$NA, (NANP)$_3$NA, and (NANP)$_6$. The model with the highest molecular weight, (NANP)$_{40}$, as circular dichroism tests demonstrate, is without a secondary structure when in water, whilst in water-trifluoroethanol mixtures [at 2–98% vol/vol (V/V)], it assumes a structure of helical type very similar to the spiral structure as proposed by Urry for tropoelastin [D. W. Urry, Proc. Nat. Acad. Sci., U.S.A., 69, 1610 (1972)].

Also the segment of CSP repetitions is likely to be without a structure. The circumsporozoitic protein could expose its central region towards the outside of the surface membrane, into contact with a means, the blood plasma, which is highly solvating and de-structuring.

This hypothesis appears to be so more plausible if one considers that the domain of (NANP) repetitions constitutes more than one third of whole CSP; therefore, it cannot be compared to a classic proteic "loop" which, owing to is small size (about from 8 to 20 aminoacid residues), even if solvated, undergoes all of the structural conditions of the remainder of the protein it belongs to.

The biological function associated to the region of the repetitions of CSP could then consist of presenting to the immunitary system a large number of epitopes, which are highly flexible and rapidly interconvertible into one another, in order to stimulate the production of heterogeneous antibodies with a low affinity for CSP, for the ultimate purpose of eluding the immunitary response.

In view of the so obtained results, to the end of limiting the number of the configurational options of the chain, and of shifting the equilibrium of the configurations in such a way as to identify those configurations which are capable of stimulating the production of antibodies with a high affinity for CSP, and possibly neutralizing, an analogous of the (NANP)$_n$ sequence, with formula (NP)$_n$, was synthesized, which, due to its larger number of proline residues, favours in the overall more rigid chain structures.

Therefore, a purpose of the present invention is to provide immunologically active synthetic polypeptides which are capable of inducing in mammals a high-titre antibody response, useful in the sector of malaria.

Another purpose of the present invention is a process for preparing said synthetic polypeptides.

A further purpose of the present invention is the use of said sequential polypeptides for the preparation of antimalarial vaccines.

Still another purpose of the present invention is the use of said sequential polypeptides in order to prepare diagnostic kits for the determination of antisporozoitic antibodies in clinical human samples.

Still further purposes of the present invention will be clear from a reading of the text, and of the following examples.

In particular, the peptides according to the present invention are constituted by at least two consecutive repeating units of -Asn-Pro- sequence, wherein Asn is L-asparagine and Pro is L-proline.

Said peptides are preferably definable by means of the following formula:

—H-(Asn-Pro)$_n$-OH    (I)

wherein Asn and Pro have the above-reported meaning, and n has a values equal to, or higher than, 2.

According to the present invention, said peptides can be prepared by means of a process comprising:

a) the synthesis of a tetrapeptide protected at the end amino group of Asn, having the following formula:

X-Asn-Pro-Asn-Pro-OH    (II)

wherein X is an acid-labile protecting group;

b) the activation of tetrapeptide (II) by means of the reaction with halogenated derivatives of phenol, in order to form the active ester of said peptide on the end carboxy group of Pro, having the following formula:

X-Asn-Pro-Asn-Pro-OY    (III)

wherein X has the above stated meaning, and Y is the radical of the halogenated derivative of phenol;

c) the removal of the protecting group from said peptide (III) by means of acidolysis, in order to obtain the peptide HCl.H-Asn-Pro-Asn-Pro-OY    (IV)

d) the polycondensation of said peptide (IV) in the presence of an organic initiator of basic nature; and finally e) the separation by chromatography of the fraction containing the polypeptide (I) constituted by at least two consecutive repeating units with (Asn-Pro) sequence.

The (a) Step

In the (a) step of the process according to the present invention, the peptide (II) can be prepared by means of a condensation in homogeneous phase, by using one of the general techniques known in the synthesis of peptides.

Typically, the synthesis is carried out by operating in an inert (non-reactive) organic solvent in the presence of a condensation agent, such as, e.g., dicyclohexyl-carbodiimide, with proline being esterified on its end carboxy group, preferably with a benzyl group (-OBzl), and asparagine being protected at its end amino group with a protective group removable under mild acidolytic conditions.

Organic solvents suitable for the intended purpose are selected from among aliphatic hydrocarbons, chlorinated hydrocarbons, aliphatic ketones, or alkyl esters.

Specific examples for said solvents are N,N-dimethylformamide, chloroform, ethyl acetate, tetrahydrofuran.

Protecting groups for sheltering the aminic functions are generally selected from among the groups which can be removed by means of acidic hydrolysis (acidolabile groups).

Among these, particularly preferred is tert.-butyloxycarbonyl (Boc).

The temperatures at which the condensation reaction is carried out can be generally comprised within the range of from −10° to 40° C., and the corresponding times are those which are required in order to complete, or substantially complete, the reaction.

At the end, from the reaction mixture the precipitated dicyclohexyl-urea is filtered or centrifuged off, and the solvent is evaporated to dryness.

The so obtained residue, constituted by the peptide

X-Asn-Pro-OBzl in which X has the above reported meaning, is suitably washed and evaporated to dryness.

An aliquot of said dipeptide is subsequently treated with hydrochloric acid in ethyl acetate or trifluoroacetic acid, at room temperature, and in the presence of anhydrous nitrogen in order to remove the protecting group from the end amino group of L-asparagine, thus the hydrochloride of L-asparagine-L-proline esterified on its end carboxy group being obtained.

Another aliquot of the dipeptide is submitted to a treatment with a catalyst of palladium on charcoal in the presence of hydrogen, in order to remove the benzyl ester from the end carboxy group of proline, with the compound X-Asn-Pro-OH being thus obtained.

The reaction is carried out at room temperature, until the starting product has disappeared.

The catalyst is finally removed from the reaction mixture by filtration or centrifugation, and the so obtained clear solution is evaporated to dryness.

The tetrapeptide (II) is then condensed by suspending the dipeptides obtained as above reported in an organic solvent, in the presence of a condensation agent.

After separating the dicyclohexyl-urea from the reaction mixture, and evaporating the solution to dryness, the residue is purified by crystallization.

From the so obtained product, the ester group is then removed from the end carboxy group of proline, by operating as hereinabove reported, and the tetrapeptide of formula (II) is separated and purified.

The (b) Step

In the (b) step of the process according to the present invention, the peptide (II) protected at its end amino group is activated by means of the reaction with a derivative of phenol, in order to form the active ester of said peptide on the end carboxy group of Pro:

X-Asn-Pro-Asn-Pro-OY    (III)

wherein X has the above stated meaning, and Y is the radical of the halogenated derivative of phenol.

Halogenated derivatives of phenol which can be used in the process according to the present invention are the fluorinated or chlorinated phenol derivatives.

Particularly suitable for the intended purpose are pentachloro-phenol, trichloro-phenol, and pentafluoro-phenol.

The reaction of activation at the carboxy group of Pro is carried out by placing the peptide (II) and the halogenated derivative of phenol into contact with each other, in a mutual molar ratio comprised within the range of from 1 to 2 in a liquid environment in organic solvent, in the presence of a condensation agent selected from among those known in the art. The reaction is carried out at a temperature comprised within the range of from −10°°C. to 40° C., and preferably at 0° C.

Examples of organic solvents suitable for the intended purpose are selected from among N,N-dimethylformamide, ethyl acetate or tetrahydrofuran.

The condensation agent preferably used is dicyclohexyl-carbodiimide (DCCI).

At the end of the reaction, from the reaction mixture the therein formed dicyclohexyl-urea (DCU) is separated, and the solvent is evaporated off.

The obtained residue is then repeatedly triturated and washed with ethyl ether.

A product is thus obtained, with a yield of about 90%, which, at $H^1$-N.M.R. analysis, and at mass spectroscopy, shows to have the expected structure.

The (c) Step

In the (c) step of the process according to the present invention, the protecting groups linked to the end amino group of peptide (III) is removed by acidic hydrolysis.

The reaction is carried out by using trifluoroacetic acid or hydrogen chloride in an organic solvent, by operating at room temperature (20°–25° C.) for a time of about 1 hour.

Through the solution nitrogen is then bubbled for a time comprised within the range of from 1 to 3 hours, and from the reaction mixture the precipitated product is separated and is repeatedly washed and evaporated to dryness under vacuum.

The product of formula (IV) is thus obtained, with a yield of about 95%, which, at TLC analysis, appears to be homogeneous.

The (d) Step

In this step, the activated and de-protected peptide (IV) is dissolved in the liquid phase in an organic solvent, and is polycondensed in the presence of an organic initiator of basic character.

Organic initiators suitable for the intended purpose are the tertiary alkyl-amines in which the alkyl group is formed by a number of carbon atoms comprised within the range of from 1 to 4.

Triethylamine is particularly preferred.

The reaction of polycondensation is carried out in an organic solvent selected from dimethyl-sulphoxide, dimethyl-formamide or hexamethyl-phosphoramide, at temperatures comprised within the range of from $-10°$ C. to 40° C. for a time comprised within the range of from 24 hours to 6 days.

In practice, the reaction is carried out at room temperature, or at a temperature close to room temperature, and, in this case, the required times for completing or substantially completing, the reaction, are of the order of 96 hours.

When the polycondensation reaction is ended, the solution, which is very thick, is dropwise added to absolute ethyl alcohol kept with mild stirring. The resulting suspension is then evaporated to dryness under vacuum, and is re-suspended with water.

From the solution, the insoluble residue is then filtered off, and the resulting clear solution is lyophilized.

The lyophil, which is constituted by a mixture of peptides with different molecular weights, can be used as such for preparing antimalarial vaccines and diagnostic kits, or it can be fractionated, according to known general techniques, so as to obtain peptides having a narrower molecular weight (MW) distribution.

In particular, according to the present invention, the fractionation of the lyophil is carried out by means of a chromatography on a column of Sephadex(®) G-50, at a temperature comprised within the range of from 20° to 25° C., and eluting with 0.1 M acetic acid at a flow rate of 36 ml/hour.

By operating in such a way, fractions are collected and separated, which correspond to a molecular weight of 1,200, corresponding to peptides constituted, on an average, by $7\pm2$ dipeptides.

All these peptides are particularly useful for the purposes of the present invention.

Peptides $(NP)_{7\pm2}$, which on laboratory animals result to be extremely powerful immunogens, are particularly suitable.

The antibodies, produced with a high titre, recognize not only the synthetic antigen $(NP)_{7\pm2}$, but also the antigen $(NANP)_{40}$.

This results show that the $(NP)_n$ sequence contains an epitope capable of very efficaciously stimulating the B cells in the production of anti- $(NANP)_{40}$ antibodies and, probably also capable of stimulating the T-helper cells.

Such a property renders the sequential peptides of the present invention particularly useful for the development of synthetic anti-sporozoite vaccines.

The sequential peptides according to the present invention can be used as such, or they can be incorporated in a more complex vaccine, constituted by different epitopes.

The following experimental examples are illustrative of the invention, without limiting it.

EXAMPLE 1

Synthesis of tert.-butyl-oxycarbonyl-L-asparaginyl-L-proline(Boc-(Asn-Pro)$_2$-OH) peptide a) Synthesis of tert.-butyl-oxycarbonyl-L-asparaginyl-L-proline-benzyl-ester (Boc-Asn-Pro-OBzl)

To a solution (350 ml) of N,N-dimethylformamide (DMF) containing 16.2 g (120 mmoles) of 1-hydroxybenzotriazole (HOBt) and 12.12 ml (110 mmoles) of N-methyl-morpholine (NMM), 24.06 g (100 mmoles) of Hcl.Pro-OBzl and 25.5 g (110 mmoles) of Boc-Asn-OH are added.

The so obtained solution is cooled down to 0° C. and to it 22.7 g (110 mmoles) of di-cyclohexyl-carbodiimide (DCCI) dissolved in 60 ml of DMF is added. The solution is then heated up to 20° C., and is reacted with stirring for 16 hours.

At the end of said time period, the reaction mixture is filtered in order to remove the precipitated dicyclohexyl-urea (DCU), and the solvent is evaporated off to dryness.

The so obtained residue is collected in 30 ml of ethyl acetate (EtOAc) and is extracted, in succession, twice with 5 ml of an aqueous solution of NaHCO$_3$ ]5%, weight/volume (W/V)], twice with an aqueous solution of citric acid (5%, W/V), and finally with water, until in the aqueous phase a neutral pH is reached. The organic phase is then separated, the residual is thoroughly dehydrated with about 10 g of anhydrous MgSO$_4$, and is concentrated under vacuum.

By operating as hereinabove reported, a gel-like residue is obtained, which is washed with EtOAc and is triturated with 20 ml of ethyl ether (Et$_2$O) until a white solid is obtained, which is then dried under vacuum.

30.6 g (73 mmoles) (73%) is obtained of the desired product, with a melting point of 106°-108° C., and an $[\alpha]_D^{20} = -79.3$ (c, 1; MeOH).

The analytical data (TLC, HPLC and N.M.R.) confirm the identity and the purity of the obtained product.

b) Synthesis of L-asparaginyl-L-proline-benzylester hydrochloride (HCl.H-Asn-Pro-OBzl)

20.32 g (48.4 mmoles) of Boc-Asn-Pro-OBzl obtained as reported in the above (a) step is reacted with 200 ml of EtOAc saturated with HCl at 20° C. for 1 hour. After said time period, through the solution, stirred, and maintained at room temperature (20°-25° C.), anhydrous nitrogen is bubbled for about 3 hours.

A white precipitate is thus obtained, which is filtered off from the reaction mixture, is repeatedly washed with Et₂O, and is finally dried under vacuum for 20 hours.

16.4 g (45.9 mmoles) (95%) is obtained of the desired product, with an $[\alpha]_D^{20} = -50.2$ (c=1, DMF).

c) Synthesis of tert.-butyl-oxy-carbonyl-L-asparaginyl-L-proline (Boc-Asn-Pro-OH)

6 g (14.3 mmoles) of Boc-Asn-Pro-OBzl is dissolved in a mixture of 250 ml of methanol (MeOH) and 100 ml of DMF.

Into the so-obtained solution, 2.5 g of catalyst—10% Pd on activated charcoal—is suspended, and H₂ is bubbled at room temperature, until the starting product has disappeared (as determined by TLC).

The catalyst is removed from the reaction mixture by filtration on Celite, and the residual clear solution is evaporated to dryness.

5.7 g of a colourless foam is obtained. The HPLC analysis shows the presence of one single peak, with a retention time of 5.66-6 under the following experimental conditions:—a column of 25×0.26 cm in reverse phase of Lichrosorb Rp. 18, 10 μ, and an eluent constituted by a mixture of acetonitrile containing 0.1% of trifluoroacetic acid and an aqueous solution of trifluoroacetic acid (0.1%, V/V) and 1% of acetonitrile (V/V) with an initial composition of 15% of organic phase. The mixture is enriched with the organic phase, with a linear gradient which, in a 15-minute time, increases the organic phase percentage to 60%.

d) Synthesis of-tert.-butyl-oxycarbonyl-L-asparaginyl-L-prolyl-L-asparaginyl-L-proline benzylester (Boc-Asn-Pro-Asn-Pro-OBzl)

Into 250 ml of dimethyl-formamide at room temperature, 4.2 g (14.3 mmoles) of Boc-Asn-Pro-OH, 5.04 g (14.11 mmoles) of HCl.H-Asn-Pro-OBzl, 1.54 g (14.11 mmoles) of N-methyl-morpholine and 1.93 g (14.3 mmoles) of N-hydroxy-benzotriazole are dissolved. After increasing the solution to the temperature of 0° C., 30 ml of DMF containing 2.8 g (13.5 mmoles) of N,N-dicyclohexylcarbodiimide is added, and the mixture is kept stirred for 18 hours. The DCU formed is then removed by filtration, and the solution is evaporated to dryness. The so obtained residue is dissolved in 400 ml of ethyl acetate and is washed with NaHCO₃ and citric acid, as reported in the (a) step.

The organic phase is thoroughly dried over MgSO₄, is filtered and evaporated to dryness until a residue consisting of a solid, white powder is obtained.

Said solid is dissolved in ethyl acetate and is crystallized by means of the addition of ethyl ether. The fraction insoluble in ethyl acetate, recovered by filtration, is washed with ethyl ether and is evaporated to dryness under a nitrogen stream, until a white solid is obtained, which has the following characteristics: melting point 163° C., $[\alpha]_D^{20} = -94.1$ (c, 1; MeOH).

f) Synthesis of tert.-butyl-oxycarbonyl-L-asparaginyl-L-prolyl-L-asparaginyl-L-proline (Boc-Asn-Pro-Asn-Pro-OH)

To a solution constituted by 100 ml of MeOH and 10 ml of H₂O, 1.1 g (1.74 mmoles) of Boc-Asn-Pro-Asn-Pro-OBzl is added.

To said solution, 1.0 g of catalyst—10% Pd on activated charcoal—is added and H₂ is subsequently bubbled through it, until the complete hydrogenolysis of the benzylester is obtained.

At the end of the reaction, the catalyst is separated by filtration on Celite, and the residual solution is evaporated to dryness. 0.89 g (95%) of a white foam is obtained. The HPLC analysis carried out under the same conditions as reported in the (c) step shows one single peak at 5.15 minutes.

EXAMPLE 2

Synthesis of the sequential peptide Poly-(L-asparaginyl-L-prolyl-L-asparaginyl-L-proline)

a) Synthesis of tert.-butyl-oxy-carbonyl-L-asparaginyl-L-prolyl-L-asparaginyl-L-proline-pentachlorophenylester (Boc-Asn-Pro-Asn-Pro-OPCP)

0.89 g (1.65 mmoles) of Boc-Asn-Pro-Asn-Pro-OH obtained as reported in Example 1 is dissolved in 60 ml of DMF containing 0.6 g (2.26 mmoles) of pentachlorophenol.

To said solution, cooled at 0° C., 50 ml of DMF containing 0.36 g (1.7 mmoles) of DCCI is added. After 16 hours at 0° C., the precipitated DCU is separated from the reaction mixture, and the solvent is evaporated under vacuum.

The so-obtained residue is repeatedly triturated and washed with ethyl ether, until a white powder (1.19 g, 90%) is obtained, which contains, as an impurity, a small percentage (about 1% of pentachlorophenol).

The product, characterized by N.M.R. and mass spectroscopy, has the expected structure.

b) Synthesis of L-asparaginyl-L-prolyl-L-asparaginyl-L-proline-pentachlorophenylester hydrochloride (HCl, H-(Asn-Pro-Asn-Pro-OPCP)

1.19 g (1.48 mmoles) of Boc-Asn-Pro-Asn-Pro-OPCP is dissolved in 70 ml of EtOAc saturated with HCl, and the resulting solution is reacted at room temperature for 1 hour.

After bubbling nitrogen through the solution for about 3 hours, the crystalline precipitate is filtered off, said precipitate is repeatedly washed with Et₂OH, and is finally dried under vacuum for 16 hours over KOH, and for a further 24 hours over P₂O₅. In that way, 1.04 g (1.40 mmoles) (95%) is obtained of the expected product, with the following characteristics: melting point 183°-186° C.; $[\alpha]_D^{20} = -65.6$ (c, 1; MeOH).

At the TLC analysis, the product is shown to be homogeneous.

c) Synthesis of
poly-(L-asparaginyl-L-prolyl-L-asparagin-yl-L-proline), Poly-(Asn-Pro-Asn-Pro)

1.0 g (1.38 mmoles) of HCl.H-Asn-Pro-Asn-Pro-OPCP obtained as reported in the above (b) step is dissolved in 1 ml of dimethyl-sulphoxide (DMSO), admixed with 0.4 ml of triethylamine (TEA). The resulting mixture is maintained with mild stirring at 20° C. for 96 hours.

At the end of the reaction, the solution, which is very thick, is added dropwise, over a time period of about 5 minutes, into 50 ml of absolute ethanol kept with mild stirring.

The resulting suspension is evaporated to dryness under vacuum and is then suspended again with water. The insoluble residue is then filtered off from the solution, and the clear solution is submitted to chromatography on Sephadex G-50 fine grade, at a temperature of 20°–25° C., using 0.1 M acetic acid as the eluent, at a flow rate of 36 ml/hour.

Two fractions were thus obtained which, after lyophilization, respectively yielded 27 mg and 30 mg of peptide with a number of repeating (Asn-Pro) units of $7\pm2$ and $3\pm1$.

EXAMPLE 3

The capability of $(NP)_{7\pm2}$ of inducing an antibody response in animals was tested by immunizing 5-weeks old male rabbits with the above said synthetic peptide.

The specificity of the antibodies formed was determined, on the contrary, by means of an immunoenzymatic test ELISA, by using both $(NP)_{7\pm2}$ and $(NANP)_{40}$ as the antigens. In practice, 6 rabbits were inoculated by intramuscular way (one inoculum), and subcutaneous way (four inoculi), as follows: 3 rabbits were inoculated with 1 ml of phosphate buffer saline (PBS), pH 7.8, containing 1 mg of $(NP)_{7\pm2}$ and 1 ml of complete Freund's adjuvant (CFA), and three rabbits (control) were inoculated with 1 ml of PBS and 1 ml of CFA.

Twenty-one days after the first inoculum, the animals were inoculated again with the same doses and with the same modalities as above reported.

Thirty-five days after the first inoculum, to the animals 1 ml of PBS was inoculated by both intramuscular and sub-cutaneous way, which contained 1 mg of $(NP)_{7\pm2}$, admixed with 1 ml of Freund's incomplete adjuvant.

The sera of the so treated animals were drawn at the 0, 20th, 34th and 48th days, and were analysed by means of the ELISA test in order to quantify the antibodies formed, and to test their specificity.

In practice, the synthetic antigens $(NANP)_{40}$ and $(NP)_{7\pm2}$ were absorbed inside wells of slabs of polystyrene for microtitration (Nunc-immunoplate I, Nunc, Roskilde, Danemark), by distributing, per each well, 50 µl of a PBS solution containing 4 µg/ml of said antigens, and maintaining the slabs at room temperature for 16 hours.

The slabs were then washed three times with PBS-Tween (0.05% Tween 20 V/V, pH 7.4), and the aspecific binding sites were blocked by incubation at room temperature for 1 hour with PBS-Tween-1% (W/V) of milk powder.

Scalar dilutions of the rabbit serum were prepared in 100 µl of PBS-1% milk powder. Then 50 µl of each dilution was introduced into each well of the microslabs, and incubated at room temperature for 1 hour.

On completion of said time period the plates have been thrice washed with PBS-Tween and incubated again with 50 µl of anti-Ig antibody of rabbit conjugated with the radish peroxidase enzyme diluited in PBS-Tween-milk powder, at room temperature for 1 hour.

The slabs were then washed three times with PBS-Tween.

Finally, 50 µl of ortho-phenylene-diamine in methanol+hydrogen peroxide was added to the slab, and, after about 30 minutes, the absorbance of the solutions at 492 nm was determined on an ELISA reader.

The results obtained are reported in following Table I.

TABLE 1

| | ANTIBODY TITRE | |
|---|---|---|
| | Anti-$(NANP)_{40}$ | Anti-$(NP)_{7\pm2}$ |
| Before immunization | 0 | 0 |
| On the 20th day | 1:7,000 | 1:800 |
| On the 34th day | 1:20,000 | 1:3,200 |
| On the 48th day | 1:80,000 | 1:10,300 |
| Control | 0 | 0 |

On the basis of the above, the synthetic peptide $(NP)_{7\pm2}$ results to be a powerful immunogen, capable of inducing a high-titre and specific antibody response against $(NANP)_{40}$ antigen.

The present Applicant was furthermore able to observe that monoclonal anti-$(NANP)_{40}$ IgG and IgM antibodies recognize $(NP)_{7\pm2}$, thus indicating that both $(NANP)_{40}$ and said polypeptides contain sequential epitopes, and have a configuration, very similar to each other.

What is claimed is:

1. Synthetic immunologically active polypeptides which induce in mammals antibody response against the circumsporozoite protein of Plasmodium falciparum comprised of the following formula:

[-H-(Asn-Pro)$_n$-OH] H-[Asn-Pro]$_n$-OH wherein Asn is L-asparagine and Pro is L-proline, and n has a values not lower than 2.

2. Synthetic polypeptides according to claim 1, wherein n is not higher than 100.

3. Synthetic polypeptides according to claims 1 or 2, wherein n is 7.

4. The peptide H-[NP]$_n$-OH wherein n is between 2 and 100.

5. Polypeptides according to any one of claims 1 or 2 adaptable for use in the preparation of diagnostic kits for the determination of anti- P. falciparum-sporozoite antibodies on clinical human samples.

* * * * *